United States Patent
Dinten et al.

(10) Patent No.: US 6,807,249 B2
(45) Date of Patent: Oct. 19, 2004

(54) METHOD FOR USING A BONE DENSITOMETRY SYSTEM, WITH DUAL-ENERGY X-RADIATION

(75) Inventors: Jean-Marc Dinten, Lyons (FR); Christine Robert-Coutant, St. Martin d'Uriage (FR)

(73) Assignee: Commissariat a l'Energie Atomique (FR)

( * ) Notice: Subject to any disclaimer, the term of this patent is extended or adjusted under 35 U.S.C. 154(b) by 0 days.

(21) Appl. No.: 10/148,109

(22) PCT Filed: Dec. 1, 2000

(86) PCT No.: PCT/FR00/03358

§ 371 (c)(1),
(2), (4) Date: May 24, 2002

(87) PCT Pub. No.: WO01/39666

PCT Pub. Date: Jun. 7, 2001

(65) Prior Publication Data

US 2003/0026385 A1 Feb. 6, 2003

(30) Foreign Application Priority Data

Dec. 3, 1999 (FR) .............................................. 99 15275

(51) Int. Cl.⁷ ............................................. G01B 15/02
(52) U.S. Cl. ......................................................... 378/54
(58) Field of Search ..................................... 378/54–56

(56) References Cited

U.S. PATENT DOCUMENTS

| | | | | |
|---|---|---|---|---|
| 4,941,164 A | * | 7/1990 | Schuller et al. | 378/205 |
| 5,040,199 A | * | 8/1991 | Stein | 378/56 |
| 5,150,394 A | | 9/1992 | Karellas | 378/62 |
| 5,457,724 A | | 10/1995 | Toth | 378/4 |
| 5,745,544 A | | 4/1998 | Mazess | 378/56 |
| 5,778,045 A | * | 7/1998 | von Stetten et al. | 378/98.9 |
| 5,841,832 A | | 11/1998 | Mazess et al. | 378/56 |
| 5,841,833 A | * | 11/1998 | Mazess et al. | 378/98.9 |
| 5,910,972 A | * | 6/1999 | Ohkubo et al. | 378/54 |
| 6,296,387 B1 | | 10/2001 | Guillemaud | 378/207 |

FOREIGN PATENT DOCUMENTS

| | | |
|---|---|---|
| WO | WO90/10859 | 9/1990 |
| WO | WO96/35372 | 11/1996 |
| WO | WO98/36380 | 8/1998 |

OTHER PUBLICATIONS

Technical Principles of Dual Energy X–Ray Absorptiometry, Glen M. Blake and Ignac Fogelman, Seminars in Nuclear Medicin, VOL. XXVII, No. 3 (Jul.) 1997; pp. 210–228.

The Evaluation of Osteoporosis: Dual Energy X–ray Absorptiometry and Ultrasound in Clinical Practice, Second Edition, Glen M. Blake, Heinz W. Wahner, Ignac Fogelman.

(List continued on next page.)

*Primary Examiner*—Craig E. Church
(74) *Attorney, Agent, or Firm*—Hayes Soloway P.C.

(57) ABSTRACT

A process and osteodensitometry system using a dual-energy cone beam of X-rays is described. The system comprises an X-ray source capable of supplying a cone beam of X-rays with at least a first energy called the high energy and a second energy called the low energy, a two dimensional X-ray detector and electronic processor for processing images supplied by the detector. According to the process, a low energy image of a part of the anatomy of a patient, and a high energy image of the same part of the anatomy of a patient are acquired, and the images acquired at low energy and at high energy are matched before building up the map of bone densities of the part of the anatomy.

12 Claims, 5 Drawing Sheets

OTHER PUBLICATIONS

Overview of Image Matching Techniques, Christian Heipke, Apr. 23, 1999, pp. 1–11.

Market Research, Independent Survey Reveals Surprising, Disappointing Results for Lunar Users, Insights, Mar. 1999, vol. 10, No. 1, p. 11.

Normalized and Differential Colvolution, Methods for Interpolation and Filtering of Incomplete and Uncertain Data, Hans Knutsson and Carl–Frederik Westin, Computer Vision Laboratory, pp. 515–523.

Les equations aux derivees partieles en traitement des images et vision par ordinateur, PDE's in Image Processing and Computer Vision, Racid Deriche and Oliver Faugeras, pp. 551–557.

* cited by examiner

METHOD FOR USING A BONE DENSITOMETRY SYSTEM, WITH DUAL-ENERGY X-RADIATION

TECHNICAL FIELD

This invention relates to a procedure for the use of an osteodensitometry system by X-rays.

It will be remembered that osteodensitometry by X-rays is a technique for measuring bone masses and densities starting from radiographic acquisitions made at several energies.

Two energies are usually used, called "high energy" and "low energy" respectively.

Various configurations of a measurement system (X-ray source and detector) could be used to make the measurements.

A distinction is made between three families of systems depending on the type of radiation used:
- pencil beam systems that use an X-ray source collimated through a hole and a X-ray monodetector that is also collimated,
- fan beam systems that use an X-ray source collimated through a slit and a linear X-ray detector, and
- cone beam systems that use a two-dimensional X-ray detector.

More particularly, the invention relates to the implementation of osteodensitometry systems by dual energy cone beam X-radiation.

STATE OF PRIOR ART

The methodological principles of osteodensitometry by dual energy X-radiation and the main technical solutions used at the moment are defined in the following two documents which should be referred to.

[1] Technical principles of Dual Energy X-Ray Absorptiometry", G. M. Blake and I. Fogelman, Seminars in Nuclear Medicine, Vol XXVII, No. 3, July 1997, pages 210 to 228 and

[2] "The Evaluation of Osteoporosis: Dual Energy X-Ray Absorptiometry and Ultrasound in Clinical Practice", Second Edition, G. M Blake, H. W Wahner and I. Fogelman, Martin Dunitz Editor, 1999, ISBN 1-85317-472-6.

In particular, refer to chapters 3, 4 and 5 in document [2] that describes principles for the measurement of bone densities using dual energies and known systems for making these measurements.

Commercially available systems for making diagnoses and therapeutic monitoring of osteoporosis in relevant sites (spinal column, hips, forearm, whole body), are of the pencil beam and fan beam type. These systems use collimators that limit parasite radiation, and particularly scattered radiation. Furthermore, the geometry of these acquisition systems limits the geometric deformations related to the size of the detector, which in particular would result from the conicity of the X-ray beam.

Furthermore, these commercially available systems use a scanning system that uses a high energy measurement and a low energy measurement in sequence, for each position of the acquisition system. This guarantees perfect consistency between the parts of the patient that are observed in the two measurements.

Commercially available cone beam systems are only designed to make bone density measurements of peripheral parts such as the fingers, toes, hands, forearms and heels. It is more difficult to implement these cone beam systems than it is to use the other two families of systems.

Scattered radiation generated by interaction between incident X-radiation and the part of the body being studied is important and cannot be ignored. Furthermore, conicity makes the measurement dependent on the position of the part of the body considered in the image field. Furthermore, during the time in which the two-dimensional sensor is being read, the patient may have moved between the high energy measurement and the low energy measurement.

"Cone beam" type systems that are commercially available at the present time are limited to an analysis of the extremities of the human body such as the hands, forearms and heels, because these areas are not very thick and their dimensions are small. Consequently, parasite radiation is limited and positioning may be consolidated, for example by using an attachment system for a forearm or a heel.

On the other hand, if this type of cone beam systems is used for larger parts of the anatomy, and particularly the spinal cord or hips, areas that are used mainly for diagnosis and monitoring of osteoporosis, it would be necessary to take account of parasite phenomena together with the significant conicity of X-radiation and adapt to potential movements of the patient.

Osteodensitometry systems for two-dimensional areas are already known, comprising a source capable of supplying X-ray flux with at least two energies, a converter screen that can transform X-rays into visible light photons, an optical image correction system and a CCD camera, and are described in the following documents which should be referred to:

[3] U.S. Pat. No. 5,150,394, Sep. 22, 1992, "Dual Energy System for Quantitative Radiographic Imaging", (Andrew Karellas), and

[4] International application published on Nov. 14, 1996, publication No. WO 96/35372, "A System for Quantitative Radiographic Imaging", (Andrew Karellas).

PRESENTATION OF THE INVENTION

The purpose of this invention is a process for the use of an osteodensitometry system like the system described in documents [3] and [4], this process being capable of increasing the precision and reproducibility of bone density measurements in different parts of the anatomy of a patient, starting from two-dimensional radiographies of these parts of the anatomy acquired at more than one energy.

For this purpose, the invention takes account of the patient's movements between two measurements taken at different energies.

This invention does this using matching between an image acquired at high energy and an image acquired at low energy, and also (preferably) a means of helping the patient to position himself.

Specifically, the purpose of this invention is a process for the use of an osteodensitometry system by X-rays with at least two energies, with a cone beam, this system comprising an X-ray source that can provide a cone beam of X-rays at at least one first energy called the high energy, and at a second energy called the low energy and lower than the first energy, a two dimensional X-ray detector and electronic image processor for processing images supplied by this detector, this process being characterised in that the low energy image is acquired from one part of the anatomy of a patient, and to take account of the patient's movements when making bone density measurements, the high energy image of this part of the anatomy is acquired and these images acquired at low energy and high energy are matched before creating the bone density map for the part of the anatomy.

According to one particular embodiment of the process according to the invention, the following procedure is used to match the images acquired at high and low energies respectively;

sets of contours of bone areas in the part of the anatomy are extracted from these images, a search is made for an optimum plane transformation in order to match the set of contours for the image acquired at high energy with a set of contours for the image acquired at low energy (or vice versa according to one variant), this transformation is used to bring the image acquired at high energy into the coordinate system of the image acquired at low energy (or vice versa according to the above variant), and these two images are combined to determine the bone density measurement map.

According to one preferred embodiment of the process according to the invention, a radioscopy plate, in other words a plate at a low X-ray dose, is made of the part of the patient's anatomy, to help in positioning this area in the system before making the acquisitions at high and low energies.

Preferably, when the patient is examined for the first time, this low X-ray dose plate is used to retroact on the mechanics of the system in order to position the part of the anatomy with respect to the predetermined coordinate system.

Preferably, when the patient is subjected to a check-up, the plate taken at a low X-ray dose will be used to put the part of the anatomy into exactly the same position that it was in during the previous examination.

More explicitly, in the preferred embodiment, a plate with a low X-ray dose and a single energy is made of the part of the patient's anatomy before making acquisitions at low and high energies. The bone contours detected on this plate are used to determine the geometric parameters either to centre the part of the anatomy in the acquisition field for a first examination, or to position the part of the anatomy with respect to the acquisition field in the same way as in the previous examination, for an examination after the first examination. In both cases, this positioning is done by moving the patient with respect to the source-detector system, or the source-detector system with respect to the patient, by manual or automatic control.

According to one particular embodiment of the invention, a plate is made at a low X-ray dose before making the high and low energy acquisitions, in order to match the irradiation dose by varying the X-ray flux, by varying the current applied to the X-ray source used and/or the voltage applied to this source.

According to another particular embodiment, a plate with a low X-ray dose is made before making the high and low energy acquisitions, in order to automatically position masks in order to limit the irradiation area.

The possibility of using a plate before the examination (also called a prescan scout data plate) in order to "centre" the patient with is known in the field of tomography from U.S. Pat. No. 5,457,724 "Automatic field of view and patient centring determination from prescan scout data", Oct. 10, 1995.

In this patent, two single dimensional projections (fan beam) at 0° and 90° of a tomographic section of a patient are acquired, before this section is reconstructed. The points corresponding to the edges of the patient are detected in the two projections, and the position of the centre of the area and the size of the tomographic acquisition are detected. These parameters are given to the operator and he can use them to move the patient to optimise centering of the patient for the tomographic acquisition. The purpose is to obtain the best possible image quality, since tomographic systems are designed such that the maximum attenuation occurs at the centre of the acquisition area and spectrum hardening corrections are made as a function of the size of the acquisition field.

This invention makes use of radiology (using a two dimensional detector) rather than tomography (using a fan beam detector in rotation). The final image is a two dimensional projection rather than a reconstructed section. Furthermore, in the preferred embodiment, a single prior plate is used rather than two plates at 90° from each other. Furthermore, one purpose of the invention is reproducibility of the measurement of the bone mass calculated from the image, rather than the quality of the image itself. Furthermore, in tomographic systems, the patient is not recentred automatically (he is recentred automatically in height but not in width, since lateral displacement of the table is not designed or is not necessary).

"Reproducibility" is the property of the measurement instrument to give the same measurement for different examinations on the same patient (assuming a constant bone density) and on the same anatomic site. In the case of a patient whose bone mass varies with time, for example under the influence of a disease or treatment, this reproducibility property can be used to quantify these variations of the bone mass.

Furthermore, in this invention, this "prescan scout data" can be used to automatically position masks to limit the irradiation area to the bone area, which is not possible in tomography otherwise truncated projections occur. In this case, the irradiation dose received by the patient is minimised.

Remember that image matching is used in several image processing domains, for example such as stereoscopic vision, analysis of image sequences, and the fusion of modal images or images with different natures.

Different approaches have been developed, for example matching between layers of grey levels or the extraction of primitives and matching between the primitives.

The following document provides further information about this subject:

[5] "Overview of Image Matching Techniques", C. Heipke, Proceedings of OEEPE Workshop on the Application of Digital Photogrammetric Workstation, Kolb O. Editor, OEEEPE Official publications, No. 33, pages 173 to 189, 1996.

Concerning positioning of the patient, the first positioning of the patient on these pencil beam or fan beam type systems is made using a laser pointer that identifies the area to be examined starting from external morphological observations. Scanning then starts. If the patient is correctly positioned, the examination continues but if the observation of the first acquired lines on the screen shows that the positioning is not good, the operator stops everything and makes a new positioning and then restarts the examination.

Further information about this subject is given in document [2], pages 198 to 200 for the spinal cord and pages 265 to 267 for the hip.

A recent study has shown that repositioning with pencil beam type systems was necessary in 50% of cases, and that the patient had to be repositioned up to three times in about 10% of all examinations. Further information about this subject is given in the following document:

[6] Insights, vol. 10, No. 1, March 1999, pages 10 and 11 (review published by the Hologic Company), "Independent survey reveals surprising, disappointing results for Lunar users".

On known cone beam type systems used for examinations of peripheral areas, the patient is positioned using a mechanical positioning aid system, for example a handle for the forearm and a bowl shaped for the heel.

BRIEF DESCRIPTION OF THE DRAWINGS

This invention will be better understood after reading the description of example embodiments given below for information only and which is in no way restrictive, with reference to the appended drawings in which.

DETAILED DESCRIPTION OF PARTICULAR EMBODIMENTS

Figure 1:
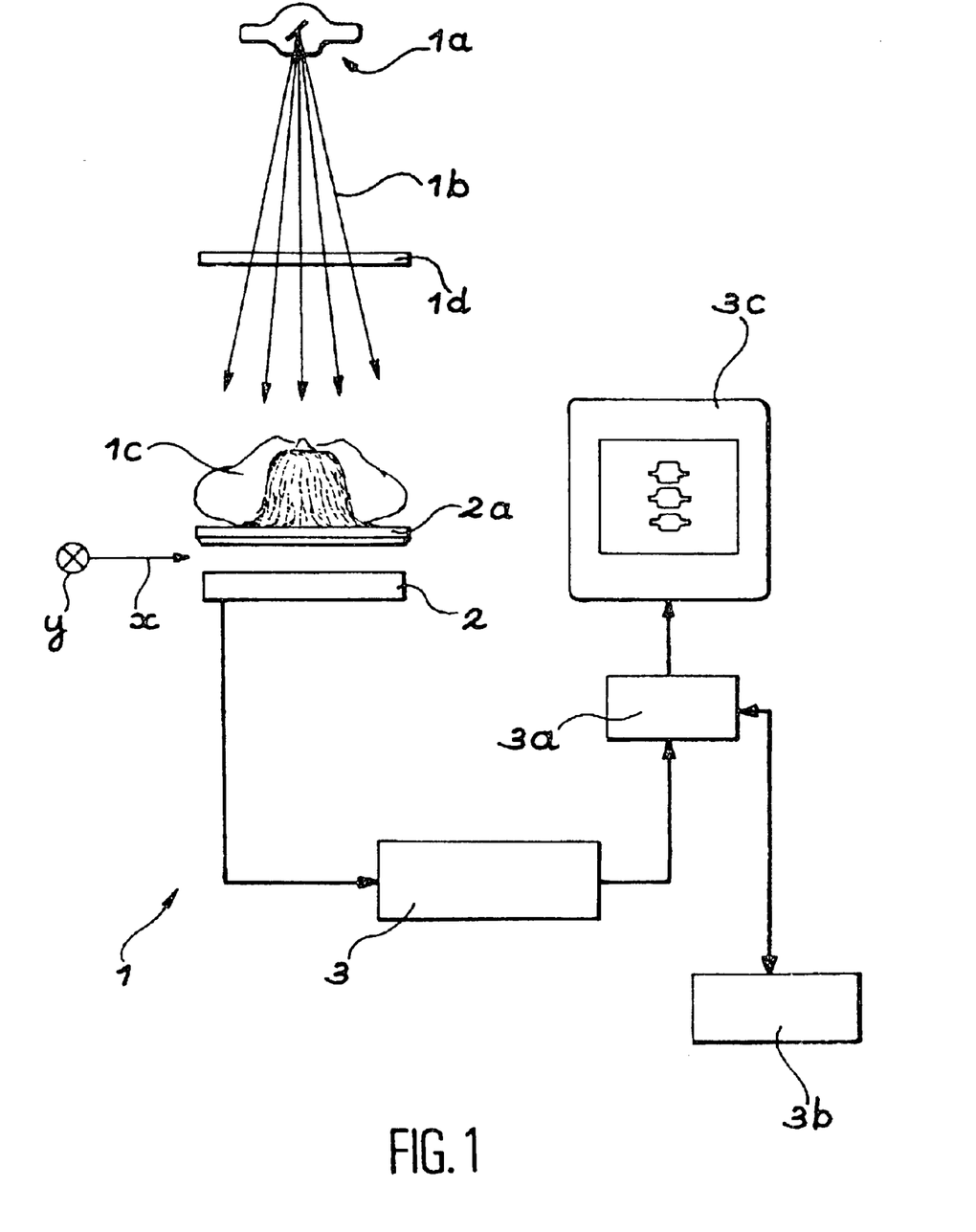
FIG. 1 is a diagrammatic view of a bone osteodensitometry system by dual energy cone beam X-radiation, that can be used for embodiment of the invention.

FIG. 1 shows a bone osteodensitometry system 1 that comprises an X-ray source 1a that can return a cone beam 1b of X-rays to the body of a patient 1c who is being examined. This source 1a can emit X-radiations corresponding to two different energy levels. These two levels are used to obtain two separate images of the patient.

A removable filter 1d can be inserted between the source 1a and the patient 1c and is used to improve the spectral qualities of the beam.

The system 1 also comprises a two-dimensional detector 2 that is very diagrammatically shown as a cross-section in FIG. 1 and is designed to detect X-rays emitted by the source after passing through the patient 1c. This detector 2 is parallel to a plane defined by two orthogonal directions x and y.

This patient is placed on an appropriate support 2a, for example a bed, that is transparent to X-rays. In the example shown in FIG. 1, the source 1a (provided with the filter 1d if required) is placed above the patient resting on the support while the detector is placed below this support.

Means not shown are provided to move the support 2a with respect to the source 1a and the detector 2 which are then fixed, or to move the source 1a and the detector 2 with respect to the support 2a which is then fixed, these displacements then being made parallel to the x and y directions.

Any type of two-dimensional detector can be used with the invention, for example a screen sensitive to X-rays and capable of directly supplying an electronic signal representing the image acquired by the detector in the form of pixels.

Instead, it would be possible to use a scintillator screen designed to receive X-rays after passing through the patient and converting these X-rays into visible light. This visible light is then sent through a mirror to a CCD sensor provided with an objective and comprising a network of light sensitive pixels.

FIG. 1 also shows a CCD or analogue type controller device 3 that reads the representation of the image supplied by the detector, pixel by pixel, and that digitises this representation. The representation thus digitised is stored in a memory 3a.

A computer 3b is provided to process the images thus memorised.

A display device 3c, for example comprising a cathode ray tube, is designed to display images before or after this processing.

This type of system can be used to implement a process according to the invention by which the following steps are applied in order to obtain good precision and good reproducibility of the bone density measurement:

the images acquired at high energy and at low energy are matched, and preferably, a first low dose radioscopy type of plate is also used to help to position the patient in the osteodensitometry system.

We will firstly consider matching between acquisition at high energy and acquisition at low energy.

It is essential that X-rays should follow the same path for each of these acquisitions in the part of the anatomy concerned, in order to build up a bone density map.

For a cone beam type system, the patient may move between the acquisition at high energy and the acquisition at low energy. One means of preventing this movement is to carry out these two acquisitions within a short time interval, less than 200 ms, as is done on pencil beam and fan beam type systems. But unlike these systems, with a cone beam type it is necessary to process two-dimensional images, in other words images comprising a large quantity of data requiring a long read time. This requires very sophisticated and very expensive technologies.

With the invention, this constraint on the speed between the two acquisitions is not applicable, since it processes the acquisitions at high and low energies afterwards.

If the two acquisitions are made within a few seconds of each other, for example about 10 seconds, the part of the anatomy may have moved slightly. If the acquisitions at high and low energies are used as they are without processing, an error is introduced in the bone density measurement. In the invention, it is proposed to overcome this disadvantage by taking account of movements of the part of the anatomy between the two acquisitions, and in order to achieve this it is proposed to match the high energy and low energy acquisitions before building up the bone density map.

We will then consider the use of a radioscopy plate for positioning the patient.

Considering that a two-dimensional sensor is used for the cone beam type system in which a single acquisition is sufficient to obtain a global view of the analysed area, it is proposed to make a low dose plate (radioscopy plate) before making the high energy and low energy acquisitions in order to help positioning the patient.

If the patient is undergoing his first examination, this radioscopy plate is used to retroact on the system mechanics (in other words to control the mechanics of the image acquisition device so that it is correctly positioned with respect to the patient or vice versa) in order to position the part of the anatomy with respect to a predetermined coordinate system.

If the examination is a patient check-up examination, the radioscopy plate is used to put the part of the anatomy into a position identical to the position in the previous examination (during which another radioscopy plate was taken).

This type of procedure can significantly improve the reproducibility of measurements made with cone beam type systems.

Due to the conicity of the beam, the measurement depends on the position of the part of the anatomy in this beam.

Good reproducibility of the examination can be achieved by using the radioscopy plate to put the part of the patient's anatomy into exactly the same position as it was in a given coordinate system or to make sure that, two different examinations are consistent with each other.

Figure 2:
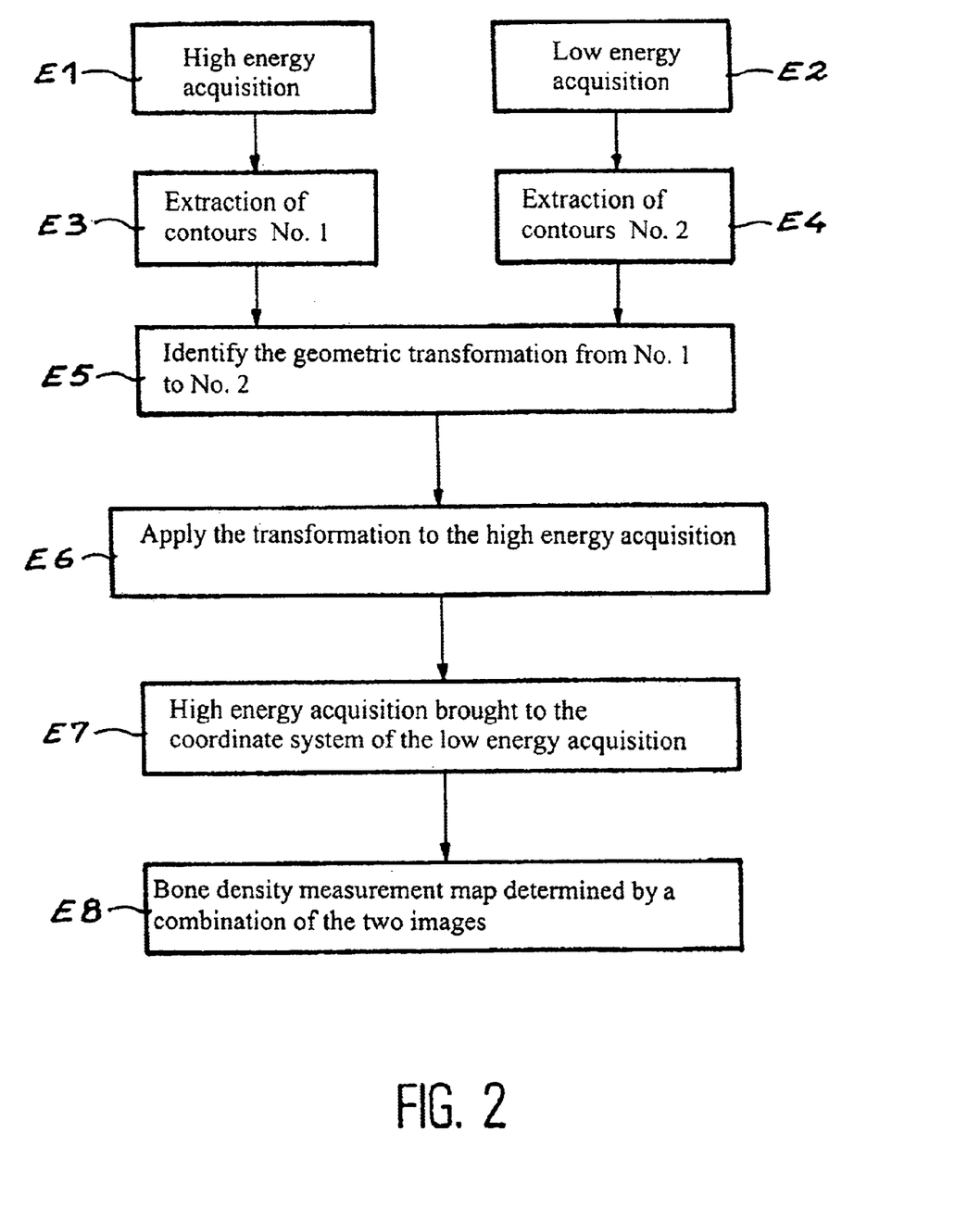
FIGS. 2 and 3 are flowcharts of procedures that are used in particular embodiments of the invention.

For example, the following procedure is used to match high energy and low energy acquisitions, as illustrated in the flowchart in FIG. 2:

1.1. the high energy and low energy acquisitions are made (steps E1 and E2);

1.2. the two sets (No. 1 and No. 2) of contours of bone areas are extracted from these two acquisitions (steps E3 and E4);

1.3. the best plane geometric transformation (for example the least squares method) (similarity, translation and rotation) is found in order to match the two sets of contours (step E5);

1.4. this transformation is used to bring the acquired high energy image into the coordinate system of the image acquired at low energy (steps E6 and E7);

1.5. these two images are combined to determine the measurement map of bone densities (step E8).

One example of the use of a radioscopy plate for positioning, for use for a patient undergoing his first examination, includes the following steps:

2.1. make a low dose plate;

2.2. extract contours of bone areas from this acquisition;

2.3. identify characteristic points in the contour map, for example identification of vertebra or marking of characteristic points on the neck of the femur;

2.4. build up the translation type function that determines the optimum position of these points with respect to a standard position defined in advance;

2.5. retroact on the positioning mechanics to return to the standard position;

2.6. make acquisitions at high and low energies.

In the case of a patient on which therapeutic monitoring is carried out, function construction step 2.4 is replaced by the following two steps:

2.4.1 recover the positions of the characteristic points in the acquisitions made during a previous examination of the patient; and 2.4.2 build up the translation type function that gives the best match of characteristic points of the radioscopy plate with respect to their position in a previous examination.

Figure 3:
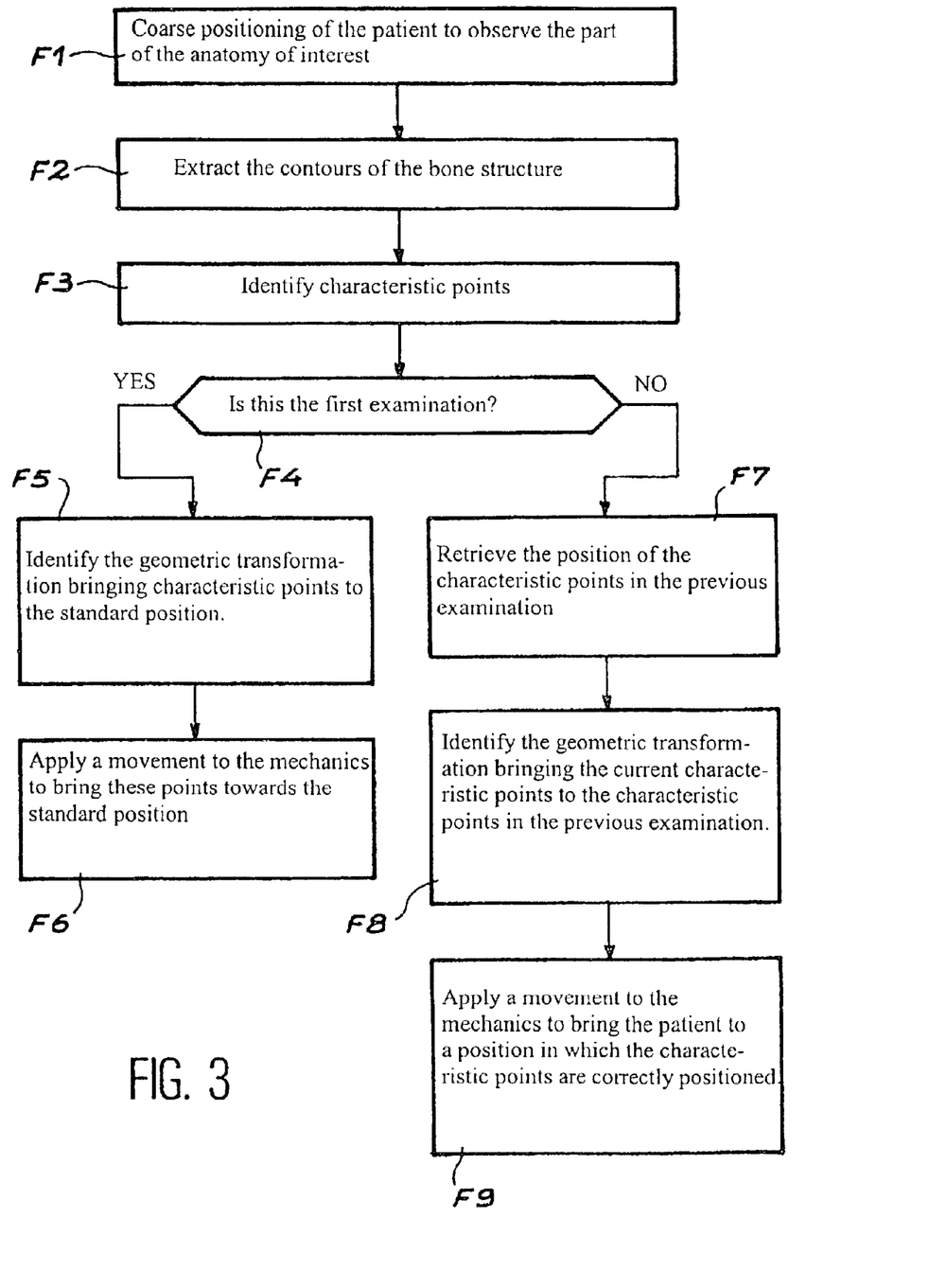

All this is illustrated on the flowchart in FIG. 3:

Step F1: the patient is put into approximately the right position to observe the part of the anatomy of interest (see 2.1)

Step F2: the contours of the bone structure are extracted (see 2.2)

Step F3: the characteristic points are identified (see 2.3)

Step F4: decide whether or not it is the first examination

If it is the first examination, go on to step F5 in which the geometric transformation bringing the characteristic points into the standard position is identified (see 2.4), and then go onto step F6 in which a movement is applied to the mechanics to bring these points into the standard position (see 2.5)

If it is not the first examination, go on to step F7 in which the position of the characteristic points in the previous examination are retrieved (see 2.4.1), and then go onto step F8 in which the geometric transformation bringing the current characteristic points towards the characteristic points in the previous examination (see 2.4.2) are identified, and then go onto step F9 in which the mechanics are moved to bring the patient into a position corresponding to a correct position of the characteristic points (see 2.5).

Furthermore, in this invention the radioscopy plate can be used to:

1/ adapt the irradiation dose by adjusting the X-ray flux by modifying the current applied to the X-rays source used and/or the voltage applied to this source 2/ automatically position masks to limit the irradiation zone, which is not possible in tomography otherwise truncated projections will be obtained.

In this way, the irradiation dose received by the patient is minimised.

The following gives further information about image processing according to a preferred embodiment of the process according to the invention.

Steps a) to e) below form the "off line" preparation steps.

a) The offset is characterised in each pixel making up an image by the acquisition of BLACK images (images without X-radiation), and the characterisation in gain is obtained by the acquisition of images at full flux at each operating energy, in other words with the maximum X radiation flux, without any object or with an object of uniform thickness, denoted PFL. A large number of acquisitions is taken and the average is calculated, in order to obtain characteristics that are only slightly affected by acquisition noise.

b) The map of pixels with defects is obtained by analysing an acquisition at full flux or an object with uniform thickness.

c) Geometric distortions are characterised by the acquisition of grid images with regularly distributed patterns; the geometric description of these grids and their images is used to build up the geometric distortion function for the system. In order to separate this effect from the conicity effect, the grids must be put into contact with the detector (reference 2 in the example in FIG. 1).

d) The geometric calibration of the system is made by the acquisition of a grid with a known geometry that is placed in positions that are perfectly identified with respect to the detector. This is a means of determining a position of the X-ray source.

e) The calibration "in density" is the same for all detection pixels (pixels obtained with detector 2 in the example in FIG. 1), since the gain differences were corrected beforehand. A ghost is used composed of a given number of elements, each element being composed of a mix of two basic materials with known thicknesses. The base materials may be a material No. 1 simulating bone and a material No. 2 simulating soft tissues. Mechanical means are used to ensure that high energy and low energy measurements are acquired perpendicular to each element, without the need to make a conicity correction. A collimation device (not shown in FIG. 1), that may for example be placed between the radiation source and the ghost or between the ghost and the detector, ensures that these measurements are free of scattered radiation. These calibration measurements are used to estimate functions that transform a (low energy measurement, high energy measurement) pair into an (equivalent thickness of basic material No. 1, equivalent thickness of basic material No. 2) pair.

These preparation steps are followed by image processing steps. A corrected image is calculated using the following formula:

corrected image=(Acquired-BLACK)/(PFL-BLACK)

where "Acquired" denotes the low energy acquisition and then the high energy acquisition.

And isolated pixels with defects are corrected using a local average calculation or a median calculation. For packets of pixels, an approach is used based on a process for correcting defects of an image from a matrix type X-ray (or γ-ray) detector (definition of a degree of confidence on different pixels and use of a normalised convolution), and this process (invented by R. Guillemaud—French patent application No. EN 98 15044, Nov. 30, 1998) is explained at the end of this description.

The position of the observed pixels is corrected starting from the distortion function identified in one of the "off-line" preparation steps, in other words step c), and a sampled image is reformed on a grid with a regular pitch by interpolation.

The low energy acquisition and the high energy acquisition are matched by extraction of a set of contours in each of the two acquisitions (contours linked to the tissue/bone interface) and determining rotation and translation parameters to convert from one set of contours to the other.

For scattered radiation, the scattered flux correction process is used in digital radiography images as described in the international patent application published on Aug. 20, 1998, publication No. WO 98/36380 (M. Darboux and J. M Dinten), and that uses a three dimensional model of parts of the anatomy, describing them as being parts composed of two materials; soft tissues (value corresponding to a proportion of fat and lean tissues for a standard individual) and bones. The dimensions of this three-dimensional model that are parallel to the projection plane are given by analysing projections. The depth dimensions are determined from an estimate of the thickness of the part of the anatomy (in an area without bones) and data provided in advance by anatomy treatises (for example position of the spinal cord with respect to the back for a posterio-anterior examination). This known process then consists of taking an approximation of the Klein and Nishina equations using this a priori description, and leads to an expression for scattered radiation as a non-linear function of the direct radiation. Further details can be found in this international patent application WO 98/36380.

For determination of the bone image, the functions that were calculated in the "off-line" step are applied to calculate a "bone" image and a "soft tissues" image. The soft tissues, with a variable proportion of fat, appear in two images at the same time and introduce a bias on the bone image. Segmentation is used to determine areas that do not contain any bone; a "base line" can be calculated on these areas corresponding to the quantity of fat tissues looking like bone. This base line may be modelled and extrapolated in areas that do not contain any bone and then extracted from the bone image.

The bone density is obtained by considering that the conicity induces a bias on these measurements, leading to a relation between reproducibility and the position of the bone area in the acquisition. This sensitivity can be limited by correcting the conicity effect on the measured area using the geometric parameters of the acquisition system determined in the "off-line" step. The bone density measurement itself is not affected (or is only slightly affected due to the discretisation) by the conicity effect.

We will now explain the process for correction of defects in an image originating from a matrix type X-ray (or γ-ray) detector.

This process is called the "PCD process" in the following, to avoid any confusion with this invention.

This PCD process is a process for correction of X or γ image defects based on the construction of a confidence map containing confidence indexes (continuous between 0 and 1) of all pixels in the detector.

More precisely, this PCD process is a process for the correction of image defects (related to pixels with defects or pixels not measured by the detector), output from an X-ray or γ ray detector of the matrix type consisting of a calibration or detector calibration step, then a step to correct pixels with defects in the image to be corrected. The PCD process is characterised by the fact that the calibration step consists of the following operations:

a)—acquisition of a black image;
b)—acquisition of at least one image of a known object;
c)—determination of at least one image with average offset and gain;
d)—acquisition of at least one image of the object to be measured with a uniform attenuation when the detector is of the X-ray type and uniform emission when it is of the γ ray type;
e)—determination of a first average and a first standard deviation for the entire image of the object to be measured;
f)—make a first confidence map as a function of the grey level of the image pixels and the standard deviation and the average determined in e);

and in that the correction step consists of acquiring an image of the object to be measured and correcting the image of the object starting from the confidence map and the last acquired image of the object.

According to one variant of the invention, the calibration step consists of making a first confidence map after operation f), consisting of the following operations:

g)—determine a grey level gradient on the image of the known object;
h)—determine a second average and a second standard deviation, and then a second confidence map; and
i)—determine a third confidence map by taking the product, pixel by pixel, of the first and second confidence maps.

Advantageously, the first and second confidence maps are composed of all confidence indexes assigned to each pixel in the image, the confidence index of each pixel being determined as a function of the grey level of this pixel, and the standard deviation and the average of the entire image of the object to be measured.

According to one preferred embodiment of the PCD process, the step b) for acquisition of the image of a known object, is made with a uniform attenuation.

According to one variant of the PCD process, in which image defects are the result of the lack of measurements on at least one part of the image, the calibration step consists of the following steps after operation f) or after operation i):

magnify the image of the object to be measured;
add pixels with zero confidence indexes, to replace the part of the image without any measurement; and
determine a fourth confidence map, starting from the first or the third confidence map, taking account of these zero confidence indexes;

and the correction step consists of making a new acquisition of the image of the object to be measured, applying the magnification to it, and correcting the image of the object starting from the fourth confidence map and the last acquired image of the object.

We will now give a detailed description of particular embodiments of the PCD process.

The purpose of this PCD process is to correct pixels with defects or missing pixels of images from an X-ray or γ-ray detector of the matrix type composed of pixels. More precisely, this process consists of building up a confidence map starting from continuous confidence indexes between 0 and 1, and representing the confidence level assigned to each pixel in the detector. It then consists of using this confidence map to correct the defects in the matrix detector by filtering, such as the KNUTSSON filter described later, or a filter by partial differential equations (PDE).

According to the PCD process, the detection of pixels with defects is continuous rather than binary, which enables more precise processing at boundaries between areas of pixels with defects.

The PCD process includes two main steps, namely:

a detector calibration step that consists of acquiring one or several images of a known reference object; then using these images to detect pixels with defects, then determining the confidence map grouping all confidence indexes of all pixels in the image; and a correction step that consists of using the confidence map to correct the image of the object to be measured by filtering, using a filter like that proposed by KNUTSSON.

In general, pixels with defects are detected by the acquisition of one or several images of a known reference object, which preferably has a uniform attenuation.

If there are no pixels with defects on the detector, the image obtained is uniform except for the noise generated by X or γ photons, and the detection and conversion of these X or γ rays into numeric values.

If there are pixels with defects on the detector, these pixels with defects are detected from a statistical analysis of the calibration image obtained and the corresponding gradient image, since a pixel with defects either has an aberrant value or a high gradient. When pixels with defects are detected, a confidence index that varies continuously between 0 and 1 is assigned to each of these pixels.

The case of detection of defects defined by a difference from the average for a uniform image and the case of detection of defects by a pixel with a high gradient for an acquisition that is a priori uniform, can be combined; these two criteria are combined using the product of the two confidence maps each made on a different criterion.

In this PCD process, the justified assumption is made that the distribution of pixels with defects is stable with time. Therefore, the defects will be visible on all images acquired on the device. The correction of pixels with defects is specific to the detector rather than to the observed image. It fills in the missing information making the best use of information supplied by nearby pixels and ensuring that the information is continuous.

The images thus corrected are easier to use by an operator for an objective, and particularly for a diagnosis.

Figure 4:
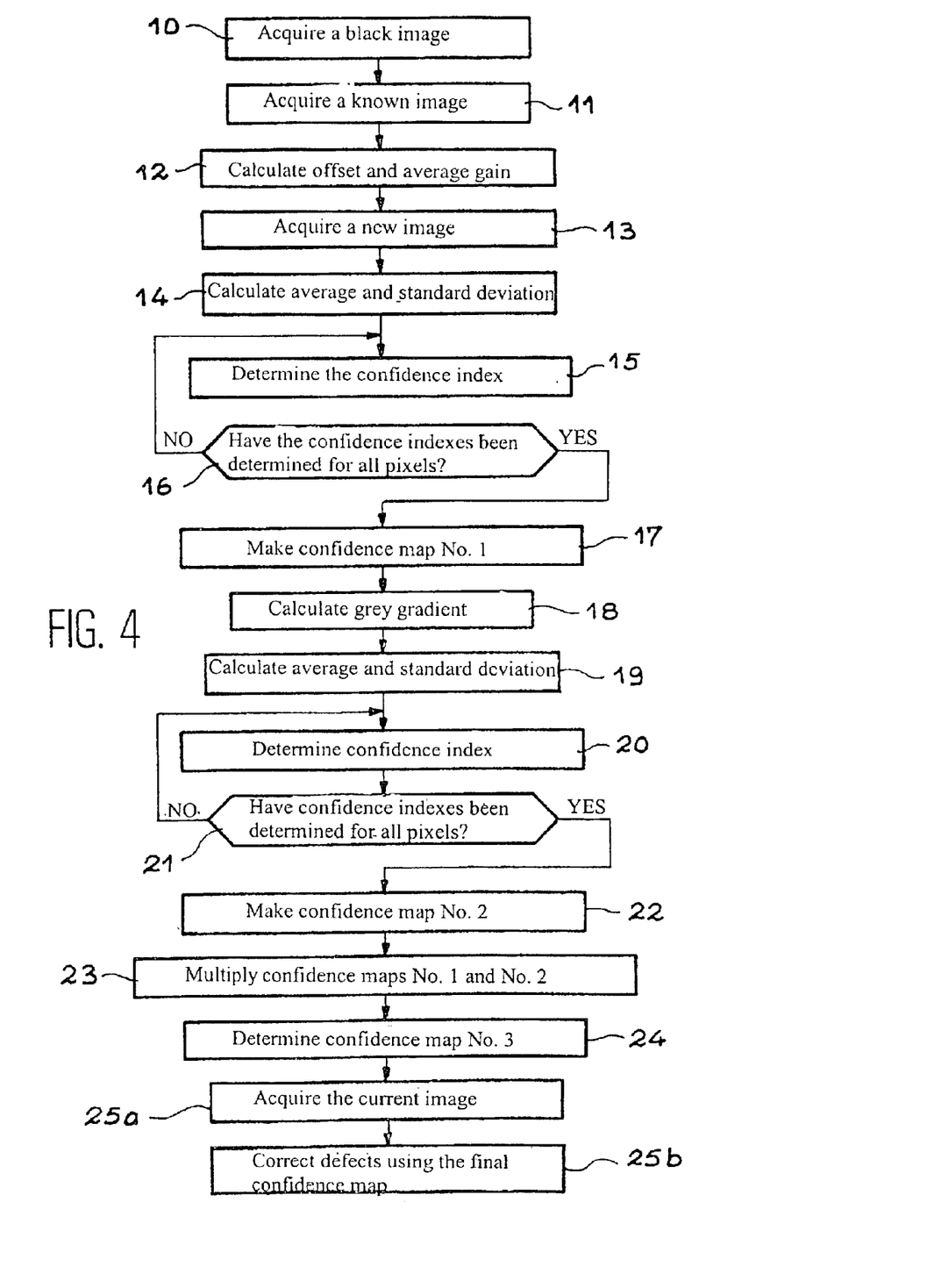
FIG. 4 shows the functional diagram of an advantageous embodiment of a process for correction of defects in an image that can be used in this invention.

FIG. 4 diagrammatically shows the functional diagram of the main steps of the PCD process. More precisely, the PCD process comprises a step 10 for the acquisition of one or several black images, in other words images made in the dark without the emission of any X-rays. This acquisition of black images is used to measure the noise of the electronics of the read device associated with the detector.

The PCD process then consists of a step 11 for acquisition of one or several images of a known reference object. This acquisition of reference images is made preferably with a uniform attenuation in the case of an X-ray detector.

The next step in the PCD process, reference 12, consists of calculating average offset and gain images Moy_N and Moy_G, where:

$$Moy\_N = 1/n \sum_{l}^{n} Nn$$

and $$Moy\_G = 1/n \sum_{l}^{n} (Gn - Moy\_N)$$

where Gn represents images of the known reference object, Nn represents black images, and n is the number of images acquired in step 10 and in step 11.

The PCD process continues with a step 13 that consists of acquiring an image Im of the object to be measured, called "new image acquisition". This acquisition is made for a uniform attenuation in the case of an X-ray detector. This image Im is then corrected for the offset and the gain as follows:

$$Im\_cor(x, y) = K \cdot \left( \frac{Im - Moy\_N}{Moy\_G} \right)$$

where K is a constant chosen by the user and its sole purpose is to define the grey level dynamics to code the value of the pixels of the corrected image.

However, the offset and the gain correction may be made using methods other than the method described above, for example using a series of object with different attenuations.

The next step 14 then consists of determining the standard deviation (or variance) and the average on the corrected image Im_cor. This average and this variance are calculated on the image corrected for the offset. The average is determined by:

$$Moy = 1/\text{number-pixel} \sum_{x} \sum_{y} Im\_cor(x, y)$$

and the variance is determined by:

$$Var = 1/\text{number\_pixel} \sum_{x} \sum_{y} (Im\_cor(x, y) - Moy)^2.$$

These values of the average and variance could be refined by eliminating the effect of aberrant points. This is done by recalculating the variance and the average of the image only for pixels for which the differences of the value from the average Moy is less than the square root of the variance by a percentage x %, where x is defined by the operator.

The PCD process is continued with a step 15 that consists of determining the confidence index of each pixel of the detector. In other words, a confidence index that is a continuous function between 0 and 1 is calculated for each pixel of the image as a function of the value of the grey level of the pixel, the variance and the average determined for the corrected image. More precisely, the confidence index is determined by:

the grey level of the pixel, determined according to the normalisation of the grey levels of all pixels in order to obtain a normal distribution:

$$norm(x, y) = \left| \frac{Im\_cor - (x, y) - Moy}{Var} \right|$$

the transformation of the value by the distribution function F of the normal law:

$$F(u) = \frac{1}{\sqrt{2\pi}} \int_{-\infty}^{u} e^{-y^2/2} dy$$

to obtain a distance called a "normal" distance:

dist_norm(x,y)=F(norm(x,y))

the calculation of the pixel confidence index:

CI(x,y)=2 (1−dist_norm(x,y)).

The confidence index is equal to 1 for a pixel for which the initial grey level is close to the average Moy; the confidence index becomes closer to zero as the difference between the value of the grey level of the pixel and the average value Moy increases.

The PCD process continues by a test 16 that consists of checking if all confidence indexes of all pixels on the detector have been actually determined. If they have not, a step is taken to continue determination of the confidence intervals in step 15. If they have, the PCD process continues with step 17 that consists of making a first confidence map C1. This confidence map includes all confidence indexes determined in step 15.

The PCD process continues with a step 18 that consists of determining the grey levels gradient of the image, on the initial image Im determined in step 13. More precisely, this step consists of:

calculating the image of the gradient grad_x(x,y,) along the direction, of the image corrected in 13, for example by convolution of the image Im_cor by a kernel $$\begin{bmatrix} -1 & 0 & 1 \\ -2 & 0 & 2 \\ -1 & 0 & 1 \end{bmatrix};$$

calculating an image of the gradient grad_y(x,y), along the y direction of the Im_cor image, for example by convolution of the image Im_cor by a a kernel $$\begin{bmatrix} -1 & -2 & -1 \\ 0 & 0 & 0 \\ 1 & 2 & 1 \end{bmatrix};$$

calculating the modulus of the gradient using the following expression:

Mod_grad (x,y)=√(grad_x,y)²+(grad_y(x,y)²

The PCD process continues with a step 19 to calculate the variance and the average of the gradient image obtained in step 18.

The variance and the average of the gradient image are determined with the following equations, respectively:

$$Moy\_grad = 1/\text{number-pixel} \sum_x \sum_y Mod\_Grad(x, y)$$

$$Var\_grad = 1 \text{ number\_pixel} \sum_x \sum_y (Mod\_grad(x, y) - Moy\_grad)^2$$

These variance and average values can possibly be improved by eliminating the aberrant points effect, as explained above for the calculation of the first variance and the first average in step 14.

The PCD process continues with a step 20) that consists of determining the confidence index of each pixel in the detector, starting from its grey level and the average and variance values determined on the gradient image. In other words, the confidence index of each pixel is determined starting from:

normalisation of grey levels for all pixels, in order to obtain a normal distribution:

$$norm\_grad(x, y) = \left| \frac{Mod\_grad(x, y) - Moy\_grad}{Var\_grad} \right|$$

transformation of the value by the normal law distribution function F, $$F(u) = \frac{1}{\sqrt{2\pi}} \int_{-\infty}^{u} e^{-y^2/2} dy$$

to obtain a "normal distance":

dist−norm_grad(x,y)=F(norm_grad(x,y))

calculation of the pixel confidence index using:

C2(x,y)=2(1−dist_norm_grad(x,y)).

The PCD process then comprises a test 21 that consists of checking that the confidence index of each pixel in the detector has actually been determined. As long as this is not true, step 20 is reinitialised for each pixel. When the confidence index for each pixel has been determined, the PCD process continues with a step 22 that consists of making a second confidence map C2 that includes all confidence indexes of all pixels in the detector determined in step 20.

The PCD process then continues with a step 23 that consists of multiplying the first and the second confidence maps, in order to obtain a third confidence map C3 (step 24). The confidence indexes of this third map are used to correct pixels with defects in the image of the object to be measured (step 25); each pixel with defects is replaced by the confidence index that corresponds to it on the confidence map C3. This third confidence map, called the final confidence map, is determined from the following equation:

C_final(x,y)=C1(x,y)·C2(x,y).

The detector is only calibrated once. The acquisition of several images can then be made on the detector and they can be corrected without needing to recalibrate the detector.

The correction step 25 consists firstly of acquiring an image of the object (25a) called a current image. The image correction step 25b can be made by filtering, using a filter such as that proposed by KNUTSSON, using the final confidence map calculated in the calibration step 24. This filter is described particularly in the document by H.

KNUTSSON and C. WESTING, "Normalised and Differential Convolution, Method for Interpolation and Filtering of Incomplete and Uncertain Data", Proceedings CVPR 93, pp 515–523, New York 1993.

In the simplest case (order 0), the method can be summarised as follows:
an image I is considered, which may for example be an image acquired on the detector X;
it is also considered that there is a confidence image C on the pixels of the image;
a new image filt_I can then be built up as follows:

filt_I=(I.C)*a/C*a where
"." and "1" are the pixel by pixel image multiplication and division operators of an image;
"*" is the convolution operator;
a is the following convolution kernel:

$$a = r^{-\alpha}\cos^\beta\left(\frac{\pi r}{2r_{max}}\right)$$

or 0 for $r \geq r_{max}$

The filt_I image thus obtained is an image for which:
the effect of the treatment on areas for which the confidence index is uniform is equivalent to a filter;
the effect of the treatment for pixels for which the confidence is less than their neighbours is a "soft interpolation", with a new value that will depend largely on nearby pixels with high confidence.

The shape and the size of the convolution kernel should be adapted to the size (minimum diameter) of the defects that are to be corrected.

Filtering according to the KNUTSSON method can be used to correct image defects by making the best use of information supplied by correct pixels in the image. Furthermore, the proposed PCD process consists of combining the initial image and the corrected image in order to create a new corrected image weighted by the confidence indexes, in order to avoid introducing a filtering effect even in correct areas in which confidence on the pixels is good. This is represented by the following equation:

Corr_I=Im.C_final+(1−C_final).filt_I, where filt_I is the image filtered using the KNUTSSON method.

Pixels with defects can be corrected from the third confidence map using other filtering methods, such as the filtering method using partial differential equations described in the document published by R. DE RICHES and O. FAUGERAS entitled "Les équations aux dérivés partielles en traitement des images et vision par ordinateur" ("Partial differential equations for image processing and computer visioning") published in the "Traitement du signal" (Signal Processing) review volume 13, No. 6, February 1996.

Figure 5:
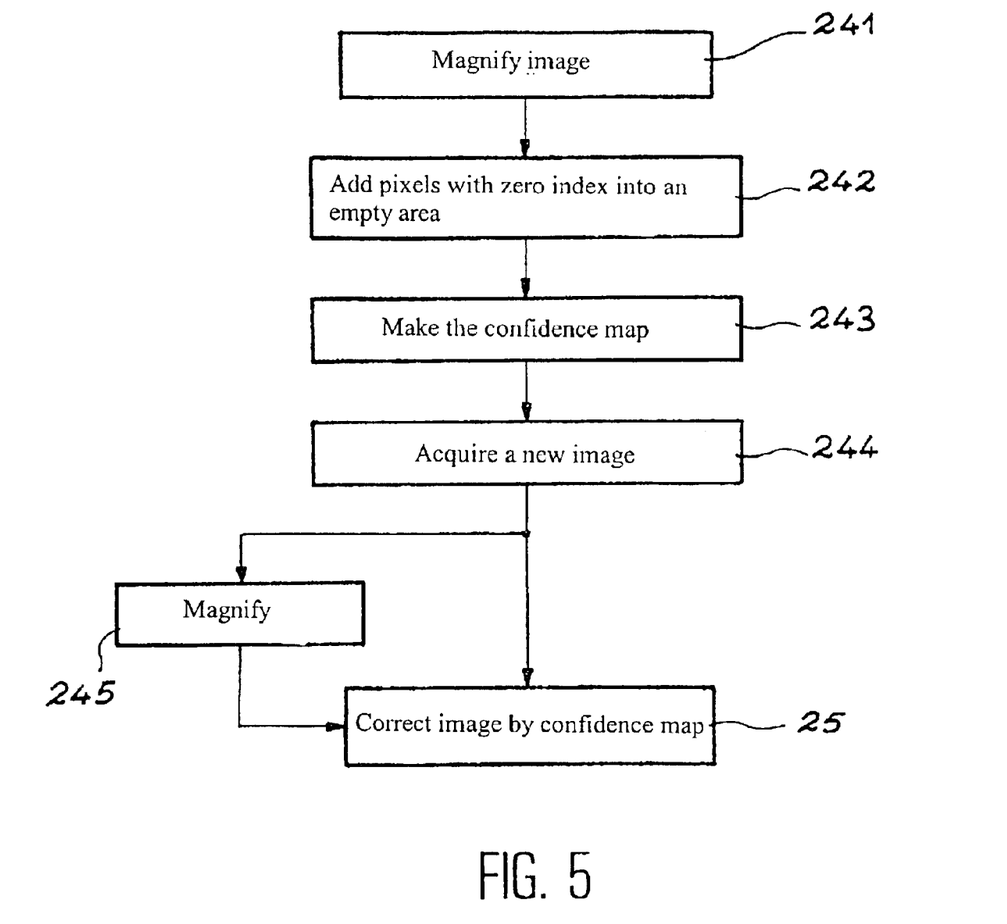
FIG. 5 shows the functional diagram of a variant of this advantageous embodiment of the process for correction of defects in an image, that can also be used in this invention.

A variant of the PCD process relates to the case in which image defects are due to the lack of measurement on one or several areas of the detector. In this case, the PCD process consists of carrying out additional steps after step 24 to determine the third confidence map. These steps are shown in FIG. 5.

In this variant, the PCD process comprises a step 241 that consist of magnifying the image of the object in order to introduce pixel areas for which there are no measurements (or missing pixels) in which the detector was unable to make a measurement. The acquired image is smaller than the image that would have been acquired with a detector capable of detecting over its entire area. A step 242 then consists of adding pixels with zero confidence indexes in these areas. A step 243 then consists of making a fourth confidence map that takes account of the zero confidence indexes of pixels in the area without a measurement. This fourth confidence map is then considered to be the final map.

When the detector has been calibrated, a step 244 is then carried out to make a new image acquisition of the object to be measured, or the current image. This current image is magnified (step 245) and then corrected. The image is corrected using this magnified current image, applying the fourth confidence map in the previously described step 25.

In other words, this variant consists of introducing areas without information, in other words pixels for which the detector was unable to make a measurement, into the final confidence image obtained in step 24; this is done by increasing the size of the confidence image. This is done by cutting the image at the missing areas and adding pixels with zero confidence indexes to fill in the gaps in the image.

What is claimed is:

1. A process for use of an osteodensitometry system using a cone beam of X-rays with at least two energies, this system comprising an X-ray source capable of supplying a cone X-ray beam with at least a first energy called the high energy and a second energy called the low energy and less than the first energy, a two dimensional X-ray detector and electronic processor for processing images supplied by this detector, this process being characterised in that the low energy image of a part of the anatomy of a patient is acquired, and the high energy image of this part of the anatomy is acquired, and these images acquired at low energy and at high energy are matched before building up the map of bone densities of the part of the anatomy, in order to take patient movements into account in the bone density measurements, wherein the following procedure is used to match the images acquired at high and low energies respectively:
sets of contours of bone areas in the part of the anatomy are respectively extracted from these images,
a search is made for an optimum plane transformation in order to match the set of contours for the image acquired at high energy with a set of contours for the image acquired at low energy,
this transformation is used to bring the image acquired at high energy into the coordinate system of the image acquired at low energy, and
these two images are combined to determine the bone density measurement map.

2. The process according to claim 1, in which a plate with a low X-ray dose is made of the part of the anatomy of the patient, to help in positioning this part in the system, before making the acquisitions at high and low energies.

3. The process according to claim 2, in which, when the patient is examined for the first time, the low X-ray dose plate is used for a feedback on the mechanics of the system in order to position the part of the anatomy with respect to a predetermined coordinate system.

4. The process according to claim 2, in which, when the patient is subjected to a check-up examination, the plate taken at a low X-ray dose is used to put the part of the anatomy into exactly the same position that it was in during the previous examination.

5. The process according to claim 1, in which a plate with a low X-ray dose is made before making acquisitions at low and high energies, in order to adapt the irradiation dose by adjusting the X-ray flux by modifying the current applied to the X-ray source used and/or the voltage applied to this source.

6. The process according to claim 1, in which a plate with a low X-ray dose is made before making the high and low energy acquisitions, in order to automatically position masks in order to limit the irradiation area.

7. A process for use of an osteodensitometry system using a cone beam of X-rays with at least two energies, this system comprising an X-ray source capable of supplying a cone X-ray beam with at least a first energy called the high energy and a second energy called the low energy and less than the first energy, a two dimensional X-ray detector and electronic processor for processing images supplied by this detector, this process being characterised in that the low energy image of a part of the anatomy of a patient is acquired, and the high energy image of this part of the anatomy is acquired, and these images acquired at low energy and at high energy are matched before building up the map of bone densities of the part of the anatomy, in order to take patient movements into account in the bone density measurements, wherein the following process is used to match the images acquired at high and low energies respectively:

sets of contours of bone areas in the part of the anatomy are respectively extracted from these images, a search is made for an optimum plane transformation in order to match the set of contours for the image acquired at low energy with a set of contours for the image acquired at high energy, this transformation is used to bring the image acquired at low energy into the coordinate system of the image acquired at high energy, and these two images are combined to determine the bone density measurement map.

8. The process according to claim 7, in which a plate with a low X-ray dose is made of the part of the anatomy of the patient, to help in positioning this part in the system, before making the acquisitions at high and low energies.

9. The process according to claim 8, in which, when the patient is examined for the first time, the low X-ray dose plate is used for a feedback on the mechanics of the system in order to position the part of the anatomy with respect to a predetermined coordinate system.

10. The process according to claim 8, in which, when the patient is subjected to a check-up examination, the plate taken at a low X-ray dose is used to put the part of the anatomy into exactly the same position that it was in during the previous examination.

11. The process according to claim 7, in which a plate with a low X-ray dose is made before making acquisitions at low and high energies, in order to adapt the irradiation dose by adjusting the X-ray flux by modifying the current applied to the X-ray source used and/or the voltage applied to this source.

12. The process according to claim 7, in which a plate with a low X-ray dose is made before making the high and low energy acquisitions, in order to automatically position masks in order to limit the irradiation area.

* * * * *